(12) United States Patent
Mundry

(10) Patent No.: US 7,873,192 B1
(45) Date of Patent: Jan. 18, 2011

(54) METHOD FOR PROVIDING A SMOOTHED IMAGE

(75) Inventor: Uwe Mundry, Mauldin, SC (US)

(73) Assignee: Imaging Sciences International LLC, Hatfield, PA (US)

( * ) Notice: Subject to any disclaimer, the term of this patent is extended or adjusted under 35 U.S.C. 154(b) by 1123 days.

(21) Appl. No.: 11/437,522

(22) Filed: May 20, 2006

Related U.S. Application Data

(60) Provisional application No. 60/682,971, filed on May 20, 2005.

(51) Int. Cl.
*G06K 9/00* (2006.01)
(52) U.S. Cl. .................................................... 382/128
(58) Field of Classification Search ......... 382/128–134; 128/920–930; 250/455–465; 356/39–49; 600/407–414, 424–426
See application file for complete search history.

(56) References Cited

U.S. PATENT DOCUMENTS

| 5,519,751 | A | 5/1996 | Yamamoto et al. |
| 6,463,167 | B1 * | 10/2002 | Feldman et al. ............. 382/128 |
| 6,757,442 | B1 * | 6/2004 | Avinash ...................... 382/274 |
| 2003/0026390 | A1 * | 2/2003 | Lutz ........................... 378/210 |

* cited by examiner

*Primary Examiner*—Samir Ahmed
*Assistant Examiner*—Atiba O Fitzpatrick
(74) *Attorney, Agent, or Firm*—Michael Best & Friedrich LLP

(57) ABSTRACT

A method of and apparatus for enhancing an array of values, which may be tomographic data, are disclosed. The values are divided into categories. Values in at least one first category are smoothed by replacing an original individual value with a new individual value determined from a plurality of neighboring values. The values in at least one second category are retained relatively unsmoothed.

16 Claims, 2 Drawing Sheets

METHOD FOR PROVIDING A SMOOTHED IMAGE

CROSS REFERENCE TO RELATED APPLICATIONS

This application claims the benefit of U.S. Provisional Patent Application No. 60/682,971, filed May 20, 2005, which is incorporated herein by reference in its entirety.

BACKGROUND

The invention relates to the visual display of information representing a variable quantity over an area having parts with distinct properties and especially, but not exclusively, to displaying x-ray images, including tomographic images, of a body part including both hard and soft tissue.

The display of information in the form of images is well known. Such images may display almost any property that has a magnitude varying over an area in the form of an image in which color or grayscale shade is used to represent the local value of the property. For example, in x-ray images, grayscale shade commonly represents tissue density, as measured by the ability of the tissue to absorb x-rays.

A set of three-dimensional data relating to a property of an object that varies over space within the object may be obtained in various ways. For example, an x-ray image of a target may be obtained by placing the target between a source of x-rays and a detector of the x-rays. In a computed tomography (CT) system, a series of x-ray images of a target are taken with the direction from the source to the detector differently oriented relative to the target. From these images, a three-dimensional representation of the density of x-ray absorbing material in the target may be reconstructed. Other methods of generating a three-dimensional dataset are known, including magnetic resonance imaging, or may be developed hereafter. From the three-dimensional data, a tomogram, which is a section in a desired plane, may be generated.

However, in a typical x-ray image both soft and hard tissues may be visible. When only one form of tissue is of interest, detail in the other form can be an unnecessary and undesirable distraction. For example, in a dental x-ray, on many occasions only the teeth and bones of the patient are of interest. In displaying an electronic x-ray image or tomogram, the grayscale can be adjusted so that the soft tissue becomes a very dark gray background. That background is typically not uniform, and the patterning on the background may be distracting.

In addition, the soft tissue image often contains significant noise, and very little actual small scale structure. Consequently, if it is desired to examine the soft tissue, the image can often be improved by removing fine detail from the soft tissue parts of the image. In the hard tissue, such as bone and teeth, fine structure is often both real and important, so it is preferred to preserve the fine detail of the image.

There is therefore a hitherto unfulfilled need for a system by which within every image, noise is removed from the soft tissue parts of an image, while retaining the crispness of imaging of small high density objects within the same image.

SUMMARY

According to one embodiment of the invention, there is provided a method and system for enhancing an array of values, comprising dividing the values into categories, smoothing values in at least one first category by replacing an original individual value with a new individual value determined from a plurality of neighboring values, and retaining the values in at least one second category relatively unsmoothed.

In a preferred embodiment, the array of values is a tomographic dataset derived from tomography of a human subject, the first category of values are densities of soft-tissue voxels, the second category of values are densities of hard-tissue voxels, and the smoothing reduces the noise in the soft tissues in the tomographic data relative to that of the hard tissues.

The invention also provides computer software arranged to enhance an array of values in accordance with the method of the invention, and computer-readable media containing such software. The software may be written to run on an otherwise conventional computer processing tomographic data.

The invention also provides data processed by the methods and systems of the invention.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION

Reference will now be made in detail to various embodiments of the present invention, examples of which are illustrated in the accompanying drawings.

Figure 1:
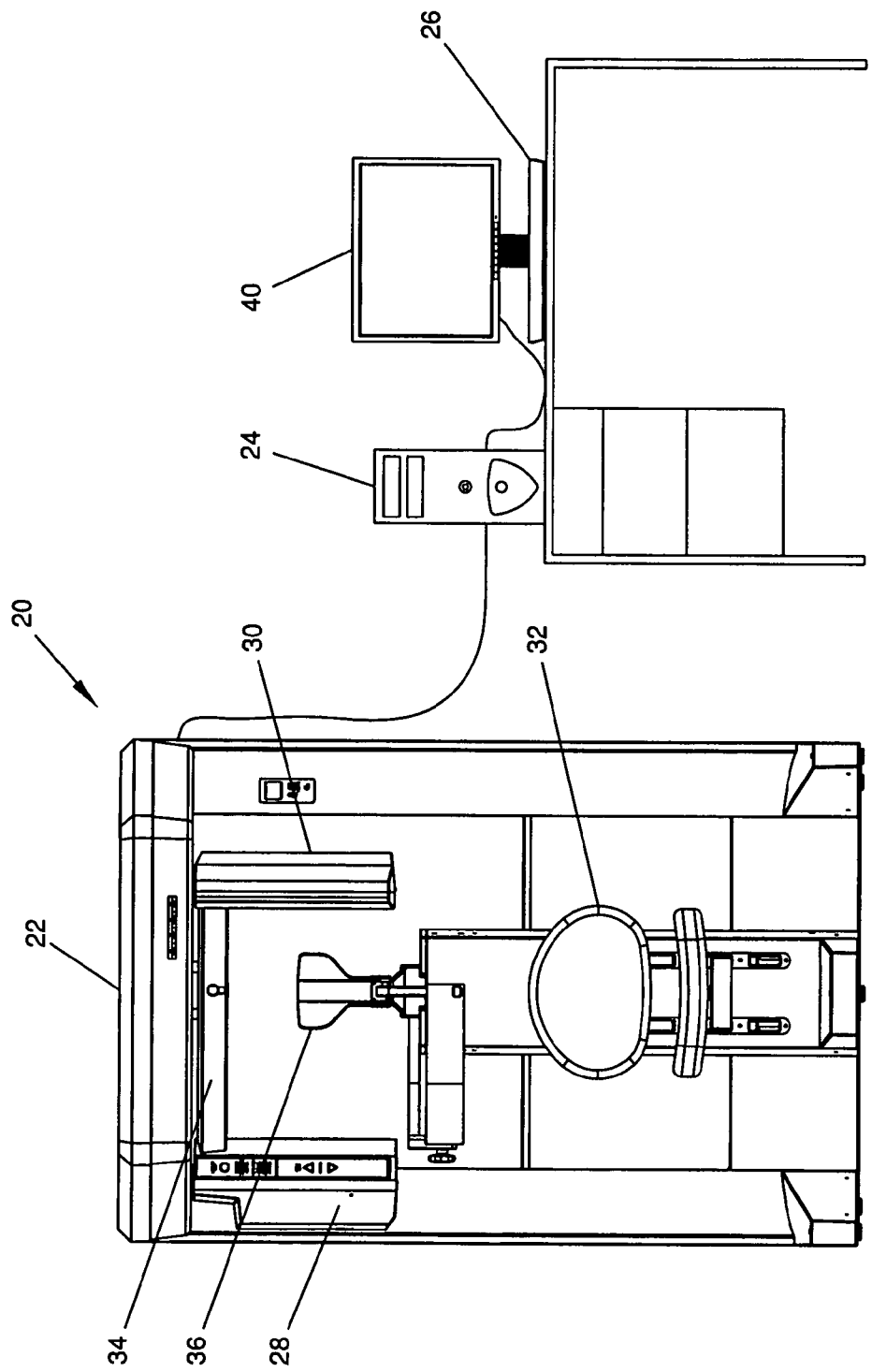
FIG. 1 is a schematic view of apparatus for generating a tomographic image.
Figure 2:
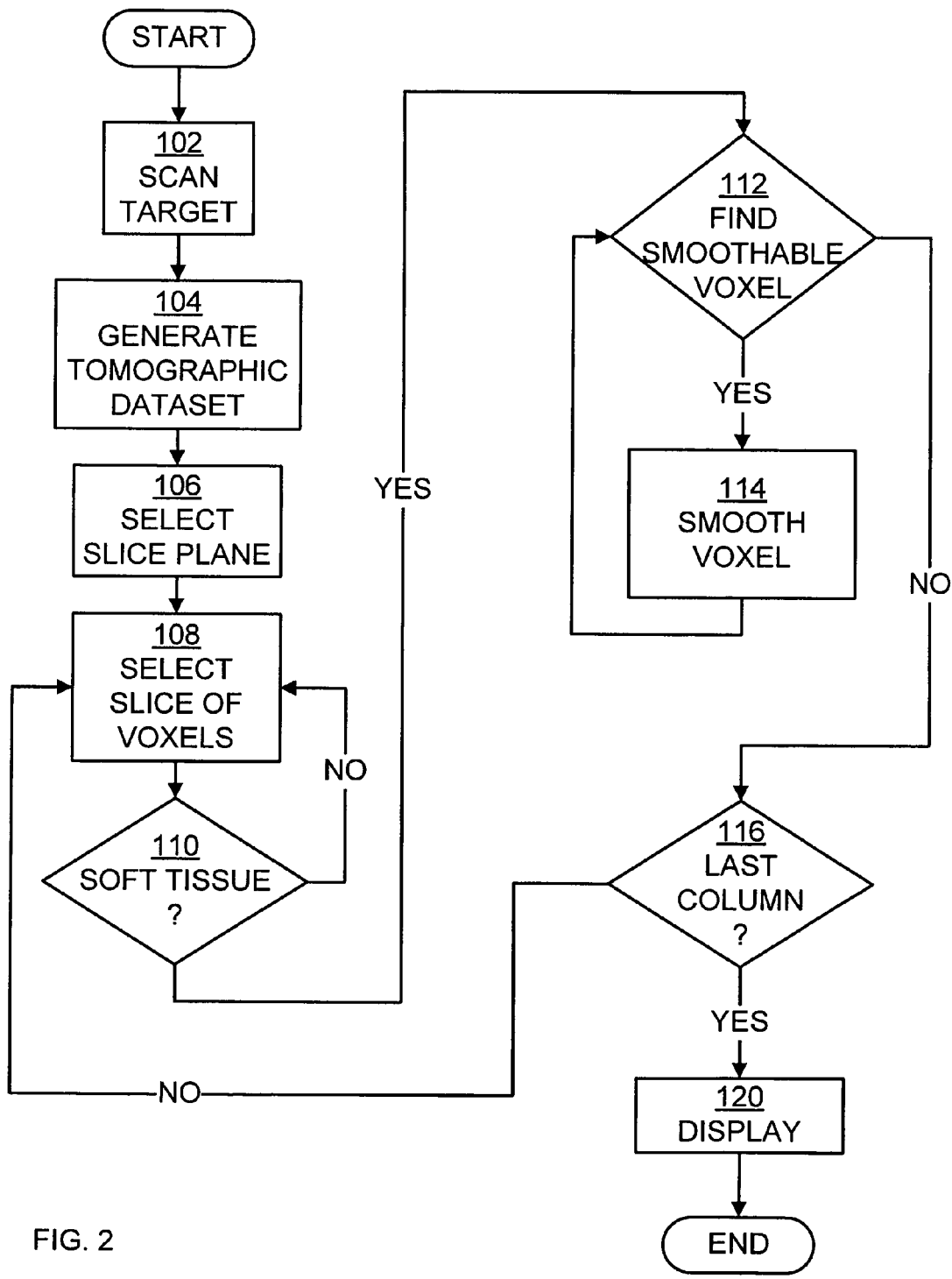
FIG. 2 is a flow chart.

Referring to the drawings, and initially to FIGS. 1 and 2, one form of tomographic apparatus according to an embodiment of the invention, indicated generally by the reference numeral 20, comprises a scanner 22 and a computer 24 controlled by a console 26. The scanner 22 comprises a source of x-rays 28, an x-ray detector 30, and a support 32 for an object to be imaged. In an embodiment, the scanner 22 is arranged to image the head, or part of the head, of a human patient (not shown), especially the jaws and teeth. The support 32 may then be a seat with a rest or restrainer 36 for the head or face (not shown) of the patient. The x-ray source 28 and detector 30 are then mounted on a rotating carrier 34 so as to circle round the position of the patient's head, while remaining aligned with one another. The x-ray detector 30 then records a stream of x-ray shadowgrams of the patient's head from different angles. The computer 24 receives the x-ray image data from the scanner 22, and calculates a 3-dimensional spatial distribution of x-ray density. Although a head x-ray scanner is shown by way of example in FIG. 1, the present method is not only applicable to x-ray head scanning, but pertains to most digital imaging devices, including whole body CT, MRI, digital x-ray, etc.

The imaging of the patient's head and calculation of the spatial distribution may be carried out by methods and apparatus already known in the art and, in the interests of conciseness, are not further described here. Suitable apparatus is available commercially, for example, the i-CAT Cone Beam 3-D Dental Imaging System from Imaging Sciences International of Hatfield, Pa.

In medical Computed Tomography, the voxels of the tomographic dataset are typically brick-shaped with a square footprint, with sides typically in the range of 0.5 mm to 1 mm. An accepted standard for definition is that a contrast difference of 0.25% or 2.5 Hounsfield Units (HU), (based on the range from air=−1000 HU to water=0 HU) between adjacent voxels should be resolvable when the density edge is at least 2.5 mm in length. For fine detail, a spatial resolution of 0.5 mm to 1 mm may be used. Because dental surgeons require very fine detail of small areas, dental tomography apparatus is available with a spatial resolution in the range of 0.1 mm to 0.4 mm. It is thus possible to reduce the spatial resolution in the soft tissue areas by a factor of 5 or 6, and still have a definition that is acceptable for medical use. The reduction may be effected either by actually merging a group of adjacent voxels or by replacing the density in each voxel with the average density of a small group of voxels centered on the voxel in question. The group of voxels may extend in one, two, or all three dimensions.

In an embodiment, the density used is an average density of a "stick" of, for example, five voxels in a line. Where the tomographic dataset is being prepared for a use in which the sections or slices will be taken primarily parallel to one plane, the stick may be perpendicular to that plane. For example, head tomograms are commonly displayed as a series of sections or slices in horizontal planes (relative to the normal position of the head of a standing or sitting person), one above the other. The stick may then be vertical. The perpendicular orientation of the stick achieves a desirable compromise between smoothing out noise and preserving any fine detail that is present in the slices.

The soft tissue may be distinguished from the hard tissue by setting a threshold density. The contrast between flesh and bone in the human body is sufficiently definite that a clear distinction is easily made. For example, in normalized Hounsfield Units, water has a value of 0 and other materials have values from −1000 (wholly transparent to x-rays) to +1000 (wholly opaque to x-rays). Fat then typically has a density just below 0 HU, soft tissue typically has a density between 0 and 100 HU, and bone typically has a density of >100 HU. The threshold density may then be set at, for example, 100 HU. Exact values may vary because Hounsfield Units are not perfectly objectively quantified, or because of differing preferences as to the treatment of materials having a density close to the threshold.

In an embodiment, at the boundary between soft and hard tissue the smoothing process stops when a group of voxels is reached that overlaps the hard tissue. Thus, when smoothing with a stick of five voxels, the third voxel from the boundary becomes an average of the first five soft-tissue voxels from the boundary, but the first and second voxels from the boundary are not averaged. That approach results in a border of unsmoothed voxels along the edge of any hard tissue, but avoids the fringing that can result from other approaches.

When merging voxels in a soft-tissue region between two hard-tissue regions, a border of unmerged voxels of variable width, but thinner than a merged voxel, may result at the boundaries with the hard-tissue regions. If the merger process starts with a merged voxel touching the boundary with the first hard-tissue region, the process ends on average half a merged voxel short of the boundary with the second hard-tissue region. As a result, the border of unmerged voxels is typically thinner along the first hard-tissue region than along the second hard-tissue region.

Referring now to FIG. 2, in one example of a process according to the invention, in step 102, the x-ray detector 30 records x-ray data of the patient's head from different angles, and in step 104 the computer 24 receives the x-ray image data from the scanner 22 and calculates a tomographic dataset representing a 3-dimensional spatial distribution of x-ray density.

In step 106, a slice plane orientation is chosen. The orientation may be conventional, for example, horizontal relative to the standing position of the patient. Where the scanner 22 is a rotary device, the slice plane orientation may be perpendicular to the primary axis of rotation of the scanner. The orientation may be specified by a user. Where the subsequent steps of the process are carried out only while generating an image for display, the slice plane orientation may be the orientation of the slice selected to be displayed.

In step 108, the process selects an initial slice of voxels parallel to the slice plane orientation. The slice may be selected by selecting each slice of voxels in the tomographic dataset in a systematic order. Alternatively, the tomographic dataset may be scanned to identify slices containing soft tissue voxels. Slices containing only hard-tissue voxels may be excluded.

In step 110, the selected slice is scanned to identify soft-tissue voxels. The process may simply confirm that soft-tissue voxels are present, or may identify the part or parts of the slice containing soft-tissue voxels. For simplicity of computation, all soft-tissue voxels may be identified. Alternatively, voxels that will not be smoothed because they are within a border along the boundary between hard and soft tissue can be excluded. For a more uniform border, parts of the slice of soft tissue voxels that lie alongside hard-tissue voxels in an adjacent column may also be excluded. Where the scan indicates that no soft-tissue voxels eligible for smoothing are present in the slice, the slice is skipped and the process returns to step 108 and selects another slice. Step 110 may alternatively be omitted. Omitting step 110 results in a simpler process but requires more computation in step 112.

In step 112, the process examines the first voxel in the selected slice, or in the part of the slice identified in step 110 as soft tissue. The process determines whether that voxel is eligible for smoothing. In an example, the process determines whether that voxel is the middle voxel of a stick of consecutive soft tissue voxels perpendicular to the slice plane. If the voxel is not eligible for smoothing, the process proceeds to the next voxel, and so on until a voxel eligible for smoothing is found. Where voxels not eligible for smoothing have been thoroughly excluded in step 110, Step 112 may simply present each remaining voxel in turn to step 114.

Once a voxel eligible for smoothing is found, in step 114 the process computes a smoothed density value from the densities of the appropriate neighboring voxels. In the example, the smoothed value may be the average of a stick of five consecutive voxels along the stick, centered on the voxel being smoothed. The average may be a simple arithmetic mean. Alternatively, the averaging may, for example, give more weight to voxels near the middle of the stick. The average may, for example, correct for non-linearity in generation of the original density values. The smoothed value may be written to a duplicate copy of the tomographic dataset, or may be overwritten on the copy from which the data for averaging were read. Where the data are overwritten, the original values can be kept in a buffer for use in smoothing voxels in neighboring slices. The process then returns to step 112 to find another voxel eligible for smoothing.

The parameters for this method should remain constant throughout the entire process, so to not introduce inhomogeneities in the images. In an embodiment, the length of the stick used for smoothing is between 1 mm and 2.5 mm, so the number of voxels forming the stick is an odd number between 1 and 2.5 mm divided by the voxel size in the direction of the length of the stick. An odd number is chosen to allow for symmetry around the center voxel. For instance, in 0.4 mm isotropic voxel datasets the maximum stick length would be 5. For a 0.2 mm dataset the maximum stick length could be 11 voxels. The maximum stick length of 2.5 mm is chosen because conventional medical CT scanners quote their spatial resolution at low contrast at or near this number, so the smoothed soft tissue image from the present process has a spatial resolution comparable to that of a conventional medical CT scanner.

If in step 112 no voxel eligible for smoothing is found before the end of the selected slice, in step 116 the process determines whether the selected slice is the last slice of voxels, or whether more slices remain. If another slice remains, the process returns to step 108 to select another slice. If the slice that has just been completed is the last slice, then the process proceeds to step 120 to display a desired image with the smoothed soft tissue.

The smoothed data may also be stored in a data file for later use.

By removing noise selectively from the soft tissue parts of the image, the user is enabled to start seeing things that might not have been seen otherwise. In the present example, the user may be able to see better visualization of soft tissue anatomy, in the sense of clinically relevant image enhancement. For example, a minute soft tissue tumor might become visible through this method that would have been lost in the noise in the unprocessed image. At the same time, the small detail in the hard tissue, which might have been blurred out in an overall smoothing of the image, is preserved. As a result, the present process can enable a combination of enhanced soft tissue visualization and undegraded hard tissue visualization.

Various modifications and variations can be made in the present invention without departing from the spirit or scope of the invention. Thus, it is intended that the present invention cover modifications and variations of this invention provided they come within the scope of the appended claims and their equivalents.

For example, in the interests of linguistic simplicity, the process has been described as smoothing one slice of voxels at a time, and one voxel at a time within each slice. Depending on the computer architecture being used, in a practical embodiment the process may carry out more than one computation in parallel. If the available level of parallelism is sufficient, some or all of the loops shown in FIG. 2 may be replaced by a single pass through a parallel system.

Where the computation for different voxels is carried out sequentially, the computation may be carried out in a different order. For example, the process has been described as being carried out slice by slice. The process could alternatively select a column of voxels parallel to the stick direction, carry out the computation for each soft tissue voxel along the column, and proceed column by column. Columns, or voxels within a slice, may be taken in a convenient order.

For example, FIG. 1 shows that the computer 24 on which the process of FIG. 2 is running is connected to the scanner 22. A single computer 24 may both control the scanner 22 and run the process of FIG. 2. Alternatively, part or all of the process of FIG. 2 may be carried out on a separate computer. The data from the scanner 22 may be transferred from computer to computer in a convenient format, for example the DICOM format, at a convenient stage of the process. The data may, for example, be transferred directly from computer to computer or may, for example, be uploaded to and downloaded from a storage server.

For example, as described with reference to FIG. 2, all the soft-tissue voxels apart from those along the borders are fully smoothed, and none of the hard-tissue voxels are smoothed at all. Alternatively, some degree of smoothing may be applied to the hard-tissue voxels, provided the smoothing does not erase the fine detail in the teeth and bones.

For example, as described with reference to FIG. 2, all the voxels are categorized as either hard tissue or soft tissue, the soft tissue voxels are smoothed (except those along the borders) and the hard tissue voxels are not smoothed. Alternatively, the voxels could be divided into more than two categories, and different smoothing algorithms could be applied to different categories. For example, medium-density and soft voxels could be smoothed with different stick lengths, and/or with different weighting along the length of the stick.

For example, when the tomographic data represent a liver scan, the user may want to leave the sharpness and detail of calcifications in place, the user may want low noise in the soft tissue, but the user may want something in between for a hyper-dense tumor, say at a density of between 50 and 80 HU.

For example, as described with reference to FIG. 2, all the soft tissue voxels are smoothed (except those along the borders) and none of the hard tissue voxels are smoothed. Alternatively, the hard tissue voxels could also be smoothed, but with a different smoothing algorithm so that the hard tissue voxels remain relatively unsmoothed as compared with the soft tissue voxels. "Relatively unsmoothed" includes not only leaving the hard tissue voxels wholly unsmoothed but also smoothing the hard tissue voxels with a smaller spatial resolution (for example, a shorter stick length) or with an algorithm that is weighted more in favor of the middle voxel or voxels, to reflect the greater importance of preserving fine detail in hard tissue.

What is claimed is:

1. A method of enhancing an image scan of an animal, the image scan including a plurality of arrays of image elements, the method comprising:

selecting a slice of image elements from the image scan;

dividing image elements of the slice into a first category representing soft tissue and a second category representing hard tissue based on a density of each of the image elements;

determining whether an image element in the first category is eligible for smoothing based on a position of the image element in a vertical array of first category image elements, the vertical array of first category of image elements positioned perpendicular to the slice;

smoothing eligible image elements in the first category by replacing an original individual value of an image element with a new individual value determined from a plurality of neighboring image elements of the vertical array when some of the plurality of neighboring image elements are in the same category as the original image element being replaced;

retaining image elements in the second category unsmoothed;

creating a border of unsmoothed image elements of the first category at an edge of the second category by selectively retaining image elements of the first category that are located near the edge of the second category unsmoothed; and creating a copy of the array of image elements, where smoothed values replace each individual value of image elements of the first category in the copy of the array of image elements.

2. The method according to claim 1, further comprising replacing the original value of an image element only when all the plurality of neighboring image elements are in the first category of image elements.

3. The method according to claim 1, further comprising replacing each of the original values of image elements in a part of the array of image elements with new individual value determined from the original values of image elements of the respective plurality of neighboring image elements.

4. The method according to claim 3, wherein the plurality of neighboring image elements from which each new value is determined comprise consecutive image elements in a column through the array of image elements centered on the location of the new value.

5. The method according to claim 1, wherein the array of image elements is a three-dimensional array.

6. The method according to claim 1 wherein the first and the second category of image elements are defined by one or more thresholds.

7. Apparatus for enhancing an image scan of an animal, the image scan including a plurality of arrays of image elements, the apparatus arranged in operation to:
   select a slice of image elements from the image scan;
   divide image elements of the slice into a first category representing soft tissue and a second category representing hard tissue based on a density of each of the image elements;
   determine whether an image element in the first category is eligible for smoothing based on a position of the image element in a vertical array of first category image elements, the vertical array of first category of image elements positioned perpendicular to the slice;
   smooth eligible image elements in the first category by replacing an original individual value of an image element with a new individual value determined from a plurality of neighboring image elements of the vertical array when some of the plurality of neighboring image elements are in the same category as the original image element being replaced;
   retain image elements in the second category unsmoothed;
   create a border of unsmoothed image elements of the first category at an edge of the second category by selectively retaining image elements of the first category that are located near the edge of the second category unsmoothed; and
   create a copy of the array of image elements, where smoothed values replace each individual value of image elements of the first category in the copy of the original array of image elements.

8. The apparatus according to claim 7, arranged to replace the original value of an image element only when all the plurality of neighboring image elements are in the first category of image elements.

9. The apparatus according to claim 7, further arranged to determine each new value of an image element from consecutive image elements in a column through the array of image elements centered on the location of the new value.

10. The apparatus according to claim 7, wherein the array of image elements is a three-dimensional array.

11. A computer program stored on a machine-readable non-transitory medium, the program comprising instructions to cause the computer to:
   select a slice of image elements generated from an image scan;
   divide image elements of the slice into a first category representing soft tissue and a second category representing hard tissue based on a density of each of the image elements;
   determine whether an image element in the first category is eligible for smoothing based on a position of the image element in a vertical array of first category image elements, the vertical array of first category of image elements positioned perpendicular to the slice;
   smooth eligible image elements in the first category by replacing an original individual value of an image element with a new individual value determined from a plurality of neighboring image element of the vertical array when some of the plurality of neighboring image elements are in the same category as the original image element being replaced;
   retain image elements in the second category unsmoothed;
   create a border of unsmoothed image elements at an edge of the second category by selectively retaining image elements of the first category that are located near the edge of the second category unsmoothed; and
   create a copy of an original array of image elements, where smoothed values replace each individual value of image elements of the first category in the copy of the original array of elements.

12. The method according to claim 1, further comprising selecting an initial array of image elements from the image scan, where the initial array is parallel to a previously selected array plane orientation.

13. The method according to claim 12, wherein determining whether an image element in the first category is eligible for smoothing further includes scanning the initial array of image elements to identify all or some of the first category image elements.

14. The method according to claim 12, wherein determining whether an image element in the first category is eligible for smoothing further includes determining whether an image element is in the middle of an array of consecutive image elements of the first category perpendicular to the array plane orientation.

15. The method according to claim 1, further comprising selecting each array of image elements in the image scan in a predetermined order.

16. The method according to claim 1, further comprising initially identifying arrays of the first category and the second category image elements in the image scan, where arrays that include only image elements of the second category are excluded from smoothing.

* * * * *